(12) United States Patent
Zdrahala et al.

(10) Patent No.: US 6,376,742 B1
(45) Date of Patent: Apr. 23, 2002

(54) IN VIVO TISSUE ENGINEERING WITH BIODEGRADABLE POLYMERS

(76) Inventors: Richard J. Zdrahala; Ivanka J. Zdrahala, both of 6825 Stonewood Ct., Eden Prairie, MN (US) 55346

( * ) Notice: Subject to any disclaimer, the term of this patent is extended or adjusted under 35 U.S.C. 154(b) by 0 days.

(21) Appl. No.: 09/505,566

(22) Filed: Feb. 17, 2000

Related U.S. Application Data

(60) Provisional application No. 60/120,723, filed on Feb. 17, 1999.

(51) Int. Cl.⁷ .......................... A61F 2/02; A61B 19/00; A61C 5/10; A61C 5/04
(52) U.S. Cl. ...................... 623/11; 623/16; 623/18; 623/66; 128/898; 433/223; 433/226
(58) Field of Search .............................. 424/93.21, 423, 424/425, 486; 433/223, 226; 435/455, 325, 382, 320; 623/16, 18, 66, 11; 128/898; 528/60, 65, 28, 75

(56) References Cited

U.S. PATENT DOCUMENTS

| | | | |
|---|---|---|---|
| 5,084,350 A | * | 1/1992 | Chang et al. ............. 428/402.2 |
| 5,556,429 A | | 9/1996 | Felt .............................. 128/898 |
| 5,769,899 A | | 6/1998 | Schwartz et al. ............. 606/77 |
| 6,140,452 A | * | 10/2000 | Felt et al. ...................... 528/60 |
| 6,224,893 B1 | * | 5/2001 | Langer et al. ............... 424/423 |

OTHER PUBLICATIONS

Riddell et al.; T–Cell mediated rejection of gene–modified HIV– specific cytoxic T lymphocytes in HIV–infected patients, 1966, Nature Medicine vol. 2, No. 2:216–223.*
Kropp et al.; Bioengineering Organs Using Small Intestinal Sumucosa Scaffolds: In Vivo Tissue–Engineering Technology, 2000, JOurnal of Endourology vol. 14,No. 1: 59–62.*
Kohn; Gene therapy for haematopoietic and lymphoid disorders, 1997, Clin. Exp. Immunol 107: 54–57.*
Zdrahala et al.; In vivo Tissue Engineering: Part 1. Concept Genesis and Guideliness for Its Realization, 1999, Journal of Biomaterials vol. 14:193–209.*

\* cited by examiner

*Primary Examiner*—Dave T. Nguyen
*Assistant Examiner*—Quang Nguyen
(74) *Attorney, Agent, or Firm*—Hoffman & Baron, LLP

(57) ABSTRACT

The present invention relates generally to the utilization of in situ polymers or copolymers to form a porous microcellular scaffold for the delivery, attachment, housing, protection, multiplication and growth of encapsulated cells. More particularly, the present invention relates to cells delivered using such a scaffold to augment, repair or replace in vivo diseased, damaged or otherwise compromised tissues or organs of a living body.

16 Claims, No Drawings

IN VIVO TISSUE ENGINEERING WITH BIODEGRADABLE POLYMERS

This application claims the benefit of U.S. Provisional Application No. 60/120,723, filed on Feb. 17. 1999.

FIELD OF THE INVENTION

The present invention relates generally to the utilization of in situ polymers or copolymers to form a porous microcellular scaffold for the delivery, attachment, housing, protection, multiplication and growth of encapsulated cells. More particularly, the present invention relates to cells delivered using such a scaffold to augment,:repair or replace in vivo diseased, damaged or otherwise compromised tissues or organs of a living body.

BACKGROUND OF RELATED TECHNOLOGY

Organ dysfunction typically represents a serious complication in the living body. A treatment for such dysfunction involves organ transplantation, but the limited availability of suitable organs, compatibility problems with the host, and difficulties with subsequent healing presents serious obstacles.

Injury, illness or degeneration of a tissue function, its assembly or, ultimately, an organ, often present life threatening situations. Surgical interventions designed to correct this including graft transplantation and whole organ transplantation from a suitable donor. These techniques suffer from the limited availability of replacement organs, compatibility problems between the foreign organ and the host, as well as problems during the healing process which must be overcome to have a viable transplant. Currently, over 70,000 patients in the United States are waiting for donor organs of all sorts: With approximately 4,000 such organs available annually, many patients will never have a chance to become a recipient.

In vitro tissue engineering, where harvested cells populate a carefully prepared scaffold which is placed into a petri dish to generate an artificial organ, addresses some of these problems. Although a relatively new technology, in vitro tissue engineering has enjoyed some success. Trauma and healing problems associated with the implantation are some of the complications which have been experienced, however.

Surgical intervention into a living body necessarily is a traumatic event. The body responds, in most cases, with defense on both acute and chronic time scales. It is well recognized that the sequence of local events related to an implantation and subsequent healing may be represented as:

Injury→Acute Inflammation→Chronic Inflammation→Granulation Tissues→Foreign Body Reaction→Fibrosis.

A serious obstacle for tissue engineered implants is the general inability of the body to accept the implant, both acutely and chronically. The body typically "walls off" the foreign body (implant) with a fibrous capsule, interfering with or preventing the intended function of the implant. Often, inflammation and bacterial infection flood the implant site with byproducts, preventing the coexistence of the host and the implant. Although recent advances in host/implant interaction biology have resulted in greater understanding of the above events, an artificial organ which does not precipitate the above response has not yet been developed.

In vitro tissue engineering involves the collection of autologous cells collected from the tissue to be augmented. These cells are used to grow an implant resembling the organ to be repaired. Among the primary objectives of tissue engineering is the integration of the engineered tissue within the patient. This is accomplished by augmenting the cells through the implantation of a supporting device or prosthesis. The replacement of a diseased organ via a suitable transplant developed through such tissue engineering presents a potentially permanent solution for curing diseased tissue.

A number of compositions and approaches are known for such purposes as preparing prosthetic implants and repairing damaged tissues and organs. Engineered tissues have been manufactured which provide new opportunities for clinical treatment. While surgical approaches involving tissue augmentation, transplantation or total replacement have proven very successful, the invasive and open nature of these procedures, the potential for infection-related complications, and the long post-procedure rehabilitation and associated costs are all inherent concerns with these procedures. The ability of implants and hosts to co-exist, as well as the trauma, inflammation healing or rejection which immediately follows implantation are all critical considerations in tissue engineering. Such concerns contribute to high health care costs in the face of patient's needs for effective and less painful treatments.

There are several critical stages to the application of tissue engineered products. First, a suitable scaffold must be generated. Cells from a potential host or donor must then be harvested and introduced to the scaffold. Cells must then propagate to populate the scaffold and the scaffold and cell assembly must be implanted to the host body to become a functioning part thereof. The implant will initially attach to and communicate with the host through a mono-cellular layer only. Traumas and subsequent healing associated with the implantation complicates the subsequent process of acceptance.

Thus, there is a need for an approach to tissue engineering which is based on minimally invasive surgical procedures. Such an approach must provide a scaffold for cellular delivery such that the cells may multiply and grow, thereby augmenting or replacing the diseased tissue which will allow the implant tissue to grow within its "natural" surroundings. The present invention, involving in vivo tissue engineering which is targeted to both soft and hard tissue repair, is directed towards meeting these and other needs.

DETAILED DESCRIPTION

In one aspect of the invention there is provided a method of in vivo tissue engineering.

In another aspect of the invention there is provided a method for the in vivo formation of a microcellular scaffold for the attachment, housing and growth of autologous, allogenous or xenogenous cells encapsulated therein.

In another aspect of the invention there is provided a method of forming such a scaffold for the in vivo augmentation repair or replacement of diseased, damaged or otherwise compromised tissues of a living body.

In still a further aspect of the present invention there is provided an implantable bioartificial tissue structure which includes a multi-phased system useful as a cell support and a cellular mass within said multi-phase system.

In the efficient attainment of its various aspects, the present invention provides a method of in vivo tissue engineering which mediates tissue healing and regeneration processes by providing, in vivo, a porous, microcellular scaffold. The scaffold is populated by propagating cells from surrounding tissue or by encapsulated harvested cells delivered to the scaffold. A minimally traumatic athroscopic surgical procedure, in combination with Bio-RIM delivery, are utilized for introduction of this system to a site to be repaired in the body.

The scaffold is populated by cells either in spontaneous or cellular augmentation. In spontaneous augmentation, the surrounding cells will spread and populate to inhabit the scaffold. In cellular augmentation, encapsulated cells are delivered to this scaffold. An athroscopic procedure is used to deliver this unique polymer/encapsulated cells delivery system to a site to be repaired. The scaffold forming polymers are desirably biodegradable.

Biodegradable polyurethanes are desirably used in this scaffold system. The polyurethanes used are selected as a result of their structural properties, the ease of their preparation, and their biocompatability. This present invention includes an in situ polymerized microcellular scaffold which is formed while the encapsulated or otherwise protected cells are being seeded therein. Once the scaffold is generated, it desirably retains its shape and internal architecture to optimize its effectiveness to perform its cell housing function. Cells from the potential host or donor are then harvested and introduced to the scaffold, where they are permitted to propagate and populate the scaffold. The scaffold and cells assembly are either fully or partially implanted into the host body and become a functioning part thereof. The implant attaches to and communicates with the host through a monocellular layer.

Autogenous cells will populate the scaffold of the present invention, which includes a system of interconnecting channels, by an attraction which is aided by bioactive species (tissue regeneration medicines). These cells will then grow to repair the damaged organ. The specific manner of implantation as well as the specific materials and cells utilized are determined on a case-by-case basis.

The scaffold used in the present invention is desirably of various shapes and desirably will have well-defined porous structure. These pores are desirably connected (in an open pore fashion) by a system of interconnecting channels. The scaffold is populated with propagating and growing cells of any suitable origin. These cells will form tissues leading to the augmented or repaired organ.

The scaffold device and method of formation include the following characteristics, steps and elements:

a) A minimally invasive surgical approach (to minimize trauma and acute host response) is the most desirable technique.

b) In vivo formation of a biodegradable microporous scaffold, via in vivo polymerization and foaming.

c) Interconnecting channels among the scaffold micropores, formed by chemical, physical-chemical or mechanical means.

d) Tissue and organ-specific cells inhabiting the scaffold in situ in a spontaneous manner which is directed by the nature and composition of the scaffold; or e) In the seeding/augmentation cellular approach, cells of any suitable origin are harvested and encapsulated in a layer of nutrient and/or mediator and implanted into the scaffold in its generation stage. Autogenic or transgenic cells, stem cells, and all other organ- or tissue-specific cells are contemplated.

f) Biodegradation of both the scaffold and cell encapsulation layer are tailored to fit the needs of all components of each individual application.

Many polymers may be used in in vivo tissue engineering. A minimally invasive approach, utilizing micro and athroscopic surgeries, will require the formation of polymer scaffold in-situ and in a reasonable time. As stated above, among polymers which may be used are biodegradable poly urethanes. Biodegradable polyurethanes are characterized by the relationship of their structure, property, and performance and the relative ease of their preparation, desirably via *Bio-RIM* technique (see R. J. Zdrahala and I. J. Zdrahala, 1999, "In Vivo Tissue Engineering, Part I. Concept Genesis and Guidelines for its Realization, J. Biomater. Applications, 14(2) p.192).

An in vivo tissue engineering system of the present invention, may have a myriad of applications. A topical application may be used for repair of the derma. Further, a plug-like implant or graft could be utilized to correct the function of diseased soft or hard tissue. The present invention contemplates repair of the liver, pancreas, cartilage or bone, among other body parts, using such an implant. In vivo formed sheets and their assemblies are intended to repair the cardiovascular system, connective tissue, or glands.

The present invention desirably employs tissue engineering techniques which effect implant/cells/host interactions and host response fields, including chemical modification of scaffold and cell encapsulation materials, gene manipulation and utilization, and harvest and implantation of stem cells.

Spontaneous or Cellular Seeding Augmentation

In the present invention, in vivo formation of the scaffold, equipped with acceptance mediating activities, increases the possibility of acceptance by the host. A minimally-sized scaffold, introduced by minimally-traumatic procedure, has a controlled porous structure and biodegradation, which in turn helps to mediate inflammation and healing. The scaffold may be formed into any desirable shape or configuration. Further, external energy fields such as heat or electromagnetic radiation may be used to assist the formation of the scaffold microporous structure.

In the spontaneous approach, the cells surrounding the scaffold are attracted by biologically active materials such as polysaccharides, proteins, peptides, genes, antigens and antibodies which are selectively incorporated into the scaffold to tether the cell receptors and to provide the needed selectivity. The interconnecting channels of the scaffold allow for cell migration, augmented by both biological and physical-chemical gradients.

Interface Gradients in Implant/Host Symbiosis

In the present invention, interface gradients between the implant and the host contribute to overcoming the monocellular layer interface often experienced in implantation of in vitro tissue engineered devices. The use of the term "interface gradients" refers to the compositional and in turn, morphological gradients within the interface layers connecting the implant to the host. The gradient composition of interface between the Hard Segment (HS) and Soft Segment (SS) domains, which determines the physical-chemical and mechanical behavior of polyurethanes, also affects their softening behavior and may cause differentiation within the regenerating tissues producing gradual, multi-layered cell attachment to the formed scaffold. (See Zdrahala, R. J. et. al, 1988, "Softening of Thermoplastic Polyurethanes: A Structure/Property Study", J.Biomater. Applications, 2(4), p.544.)

The interfacial gradients of attachment between the host and device should be considered, particularly where a significant difference between the elastic moduli of implant and surrounding tissue exists, (e.g. cartilage vs. bone).

Cells for the In Vivo Tissue Engineering

While the spontaneous population of the scaffold by host cells is a desirable way of healing augmentation and organ reconstruction, cell seeding augmentation may provide other benefits, such as flexibility. Desirably, stem cells and transgenic cells are used in cell seeding. For example, upon implantation, the stem cells undergo modification and generate a population of tissue specific cells such as mesenchymal cells, brain cells, endothelium and angiogenesis, osteoblasts, etc.

To effect seeding, appropriate cells are desirably encapsulated into a biodegradable shield sack of mediator membrane, the surface of which is modified with tethers to biodegradably attach the sack to the scaffold. The sack desirably contains nutrients for the cells to survive and propagate. Each encapsulated cell desirably forms a unit with its potential multiplication and growth. Microencapsulation technology is frequently used to encapsulate living cells, as illustrated in U.S. Pat. No. 5,084,350 to Chang and Wong, hereby incorporated by reference.

Materials

Two different groups of materials may desirably be used in the present invention for in vivo tissue engineering for the scaffold and for the cellular seeding augmentation approach using the cells encapsulation system, respectively. Although the polymers used for the scaffold and the encapsulation of the cells may differ, they must closely coexist, and consequently both materials will desirably possess the following characteristics:

a) Biodegradable, with stepwise, directed biodegradation.

b) Amenable to microphase separation and formation of distinctive domains to mimic tissue complexity.

c) Deliverable to the in vivo site, in single or multiple fashion.

d) Polymerizable by stepwise polymerization with controllable kinetics and low reaction exotherm to prevent necrosis of the surrounding tissue.

e) Does not produce any toxic or otherwise harmful reaction or decomposition byproducts.

f) Supports formation of microporous, foam-like mass in one-phase or multi-component IPN (Interpenetrating Polymer Network) systems.

g) Broad range of physical-mechanical properties to support diversity of applications.

h) All components of the system are desirably compatible; encapsulated cells are compatible with components of the scaffold and must survive delivery and fixation to the forming scaffold.

i) All the components of the system should accept, protect and timely-release mediators for cell attraction, attachment and growth.

Any polymers which exhibit at least some of these characteristics may be employed. Polyurethanes and their block copolymers and composites are particularly desirable for use in the present invention because they exhibit most of these characteristics. Polyurethanes useful in the present invention are generally block copolymers, based on alternating hard segments (HS) and soft segments (SS); these can separate into respective domains and form phase separated morphologies. These materials can be easily foamed to produce open or closed microporous cells. Alternatively excellent films and membranes can be formed. The synthesis of the polyurethanes of the present invention does not produce any appreciable byproducts. Moreover, the reaction exotherm and the kinetics of their formation can be designed and controlled. These materials also exhibit a broad and diversified Structure/Property/Performance relationship expressed by excellent range of physical-mechanical properties. Biodegradation/biodurability balance of the polyurethanes of the present invention is achievable by selection of the biodegradable intermediates.

An important aspect of the present invention concerns host body tolerance and disposal of in vivo degradation byproducts. It is desirable that biodegradability should proceed in both surface and bulk fashion. Hydrolytic and oxidative attacks will generate low molecular weight oligomers at the surface and within the bulk of the cured structure. Depending on their molecular weight, these byproducts can be filtered out by the kidneys and excreted in the urine. With respect to the molecular weight of compounds which may be removed by kidneys, 40,000 Daltons MW is generally recognized in the art as the largest size molecules which may be filtered, depending on their structure. There is, however, a possibility of material crumbling into small pieces. In addition to hydrolytic and oxidative attack, the particles, depending on their size, could be enclosed by the body in a fibrous capsule, and may be phagocytosed or may undergo additional, often autocatalyzed hydrolytic degradation to be, disposed off by the kidneys.

Application of the System

Where a cellular approach is taken, the present invention allows the use and minimally invasive surgery for in vivo site preparation and cell collection. Similar techniques may be used to deliver scaffold-building components (and when applicable, the encapsulated cells) to the prepared site to form the scaffold via a polymerization reaction. Many aspects of this process are clinically driven and thus are subject to surgical techniques. Of particular importance, however, is the in situ formation of the scaffold.

Reaction Injection Molding (RIM) is based on molecular-scale impingement mixing of two or more streams of co-reactive components needed for a polymer formation. Upon mixing, this mixture is fed to the reactor (the mold) for relatively rapid polymerization.

The Bio-RIM technique of the present invention comprises a multi-stream system which is mixed and delivered as single stream. For polyurethanes these are: (i) an is 6cyanate-terminated stream, (ii) and a hydroxy-terminated stream, along with any desired additives. Additionally, (iii) a stream containing the encapsulated cells is desired for the present invention. It is to be understood that any number of component streams may be used in the present invention.

The components are desirably kept in separate, stirred, inert atmosphere-protected and temperature-controlled environment (e.g. tanks or disposable containers). The streams are volumetrically fed into a suitably chosen impingement mixing chamber. In addition, mechanical stirring or mixing by a Kenix™-type mixer can be used to assure thorough mixing. Furthermore, a mixing chamber for gentle mechanical stirring by cone-and plate or parallel-plate assemblies may be provided for mixing-in a stream of encapsulated cells, where needed.

In-line thermocouples, together with an infrared spectrometer probe, are placed into the mixed coreactants stream to monitor the reaction kinetics of the scaffold formation. Additionally, when the system application calls for utilization of salt as a nucleating agent to assist formation of specific cell structure, the system has a provision of adding additional streams to so accommodate. Irrigation, vacuum debridement, inert gas, and various probe inlets are also desired aspects of the delivery/polymerization system.

The system of the present invention desirably comprises an in vivo formed microporous scaffold with both open and closed cells architecture. This desired aspect further comprises biologically active species to attract, tether and support cell propagation. Another desired aspect of the present invention encompasses biodegradable polymers, such as polyurethanes and their copolymers, with other polymers as encapsulation materials for selected cells which are provided to augment healing and regeneration. The scaffold of the present invention desirably has the ability to degrade in vivo in a controlled manner, without providing harmful byproducts.

Polyurethane-based Scaffold

Predominantly hydrophilic polyurethane, polyurethane-hybrids and multi-blocks (those containing several HS and SS moieties) with fast, medium or slow biodegradation rates are desirably used as scaffold materials in the present invention. The aliphatic isocyanates are desirably used to avoid the potential formation of aromatic diamines during the polyurethane hydrolysis. For effective delivery to the repair site, they are desirably provided in a liquid state at ambient conditions. The use of aromatic isocyanates, neat and in a blend form, may also be employed. A quasi-prepolymer approach assures the liquid state of the isocyanate. The formation of optimized hard segment domains and co-domains is developed by incorporation of crystallizable nucleating agents into the quasi-prepolymers.

The desired chain extenders used in the present invention are low molecular weight sugars and their derivatives. These yield biodegradability to the HS domains. In addition, N-substituted hydroxylamines, diols, triols and amines are also contemplated. Further, autocatalytic chain extenders are desirably used to augment catalysis of in vivo polymerization.

Polyester- and polycaprolactone-based polyols, polyethylene glycols, polysaccharides (starch, amylose, alginates, etc.), hydroxy- or amine-terminated lactide-, glycolide- or biodegradable hydrogel-based oligomers are desirably used as the SS intermediates. The use of glycosaminoglycan (GAG)-collagen copolymers with thermally-triggered collagen inversion, is also contemplated. The necessity that the components be maintained in a liquid state during the Bio-RIM delivery is an important consideration in the selection of intermediates. A unique microporous mass, composed of both open and closed pores and of a desired porosity is generated by using water, carbon dioxide and surfactant-like, vaporizable foaming agents.

Connective Channels For Cell Communication

The IPN approach- of the present invention, which includes admixing low viscosity/low molecular weight, easily degradable oligomers within the scaffold intermediates is desired for an open pore architecture leading to connective channels. These could be "stitched" together via labile urethane linkages (polyurethane stitching) to scaffold intermediates to assure the desired distribution. Sequential, stepwise decomposition of these oligomers and their distribution by physical-chemical processes, heat or wave energy fields, might be used.

Cell Housing

When a cell seeding augmentation approach is used, permeable film and membrane forming encapsulants with controlled biodurability are desirably used. A glycolide/lactide-co-polyol-co-polysaccharide, "polyurethane-stitched" urethane-co-polyethyleneglycol-co-polysaccharide and hydrophobic-co-polyvinylalcohol-copolysaccharide block copolymers with any other biocompatible natural or synthetic material are desirably used. These materials exhibit a film-forming capability which serves as a protective shield against the body's immune system.

Bioactive Species

The use of proteins to mediate the interface between the host and the implant is desired. For example, albumin has been evaluated and used to regulate blood compatibility. Bone Morphogenic Proteins to enhance bone regeneration in orthopedic implants are useful. Genes and gene therapy may also be used in the implant/host relationship.. The use of polysaccharides in mediating the host/implant interface is also contemplated. Anti-infectives, growth factors and other useful bioactive species are useful for incorporation into the scaffold or cell encapsulation.

Scaffold Modification by External Force Field

In vivo formation of the microporous scaffold, with a combination of closed pores (for stiffness and integrity) and open pores (for cells migration), may require external assistance of an energy field. In such a case, ultrasound, laser or similar wave-energy fields, in combination with low molecular weight additives, are desirably used for sequential foaming to control pore geometry and, in turn, the nature of the scaffold, further assisting accommodation of growing cell populations. In addition to pore size and shape modification, localized interference with the cure kinetics by unblocking the blocked isocyanate groups, micro-droplet formation and their distribution and absorption are involved.. Further, these wave-force-fields can also be used for the visualization of the scaffold, in combination with radiopaque and nuclear magnetic resonance opacity.

The polyurethane structure is desirably of block copolymer nature, based on alternating hard segments (HS) and soft segments (SS); these can separate into respective. domains and form phase separated morphologies of resultant systems. Further, they are easily foamed to produce open or closed cell, microporous foams and they form excellent films and membranes. Additionally, their synthesis does not produce any byproducts and they exhibit an excellent range of physical-mechanical properties. Their biodegradation/biodurability balance is controlled by selection of biodegradable intermediates.

The Hard Segment Intermediates

The HS determines the strength and load-bearing related properties of the copolymer. It is formed by reaction of isocyanate with a functionality greater than or equal to two chain extenders. The most desired isocyanates are those of the single molecule and quasi-prepolymer type. As a single molecule, the liquid species are desirable (e. g., hexamethylene diisocyanate (HDI), hydrogenated diphenylmethane diisocyanate (HMDI), isophorone diisocyanate (IPDI), etc). In a further desired aspect, the —NCO reactive groups are temporarily blocked to preserve their available reactivity and then unblocked by heat (e.g. from reaction exotherm) for latter stages of the scaffold formation The use of solid diphenylmethylene diisocyanate (MDI), having a melting point between 40 and 45 degrees Celsius, together with HMDI, HDI, IPDI and the like, comprise a desired aspect of the present invention, namely an isocyanate quasi-pre polymer. Such polymer is typically prepared by the reaction of stoichiometric excess of isoycanate with active hydrogen-containing low molecular weight or oligomer polymer by methods known to those skilled in the art. Based on overall stoichiometry, the quasi-prepolymer contains a mixture of NCO-terminated molecules and a single molecular isocyanate as euteticum, thereby forming the liquid intermediate. In a desired aspect of the present invention, polyethylene oxide (PEO) of molecular weight (MW) of 200 to 4000 daltons, branched or star-like PEOs of MW of 150 to 5000 daltons can be used. Furthermore, polycaprolactones (PCL) of MW of 400 to 2000 daltons, ethylene-adipate or similar polyester polyols of MW 400 to 2000, C5 and C6 carbohydrates, low molecular weight amylose or the like, may also be used. Additionally, polymeric MDI isocyanates such as RUBINATE™, 1208, 1680 or 1850 may be used (ICI Polyurethanes, West Deptfort, N.J.).

The chain extenders desirably comprise low molecular or oligomer moieties, with a functionality greater than or equal to two, terminated with groups containing active hydrogen (e.g. hydroxy or amine groups). Furthermore, they may possess autocatalytic activity when nitrogen, secondary and tertiary amines or quaternary ammonium salts are part of their structure. The following chain extenders may be used in the present invention, but this list is in no way meant to be limiting: ethylene and propylene glycols (EG and PG), diethylene glycol (DEG), butane, pentane and hexane diols (BDO, PDO and HDO), neopentyl glycol (NPG), glycerine, PEG and star-PEG of MW of 200 to 1500, dihydroxypropionic acid (DHPA), trimethylol propane (TMP), glucose and similar carbohydrates, hydroxy-terminated low MW diols-maleic or fumaric esters and diesters of lactic acid and glycolic acid oligomers, di- and tri-hydroxy ethyl amines (DHEA and THEA), n-methyl-di(ethylene glycol) amine (NMDEG), silanol-terminated (Si—OH) di- and polyfunctional low MW reactants and the like.

The Soft Segment Intermediates

The soft segment intermediates are typically determinative of the deformation-based properties of the polymer. Desired aspects of the present invention comprise biodegradable hydroxy- or amine-terminated, two or higher functionality polyols, polyesters or polysaccharides with MW ranging from 400 to 6000 daltons, including, but not limited to, adipic acid-based polyester polyols, such as FOMREZ™ materials (WITCO Chemical Co.). Polycaprolactones (PCL) with MW of 1000 to 3000 such as PCP-0200, -0240 and 0260 (Union Carbide Corp.). A glycerine started PCL, PCL copolymers with PEO, polylactides (PLA) and polyglycolides (PGA), PEO-PLA-PGA copolymers, PEO-polyvinyl alcohol (PVA)-PGA-PLA copolymers, polysaccharides such as amylose, starch and their copolymers with PEO, PLA and PGA and the like. A choice of specific SS intermediate depends on the intended application.

Catalysis

In a desired aspect of the present invention, there exists a synergistic combination of organotin such as COTIN 222 from CASCHEM Chemical Co. and tertiary amines such as triethylene diamine, e.g. the DABCO family (Air Products and Chemical Co.).

Blowing Agents

Water, saturated with carbon dioxide, air, oxygen and nitrogen or any inert gas, desirably in concentration from 1 to 10 weight percent (wt. %) is desirably used in the present invention for formation of a microcellular scaffold. Further, low boiling alcohols such as ethanol and isopropanol, as well as alcohol/water azeotropes, are used to control and/or expand the blowing intensity/temperature range expand the preferred embodiment field. Electrolyte solutions such as n-saline or Minimum Essential Medium (MEM) and introduction of fine crushed particles in their frozen state is contemplated to further control the formation of microcellular structure. A combination of the above are desirably used.

Porosity Control

For attainment of required cell size and morphology, the cellular structure may desirably be further controlled by the addition of an agent known to provide such modification. This is particularly important, for instance, when a balance between closed and open cells is required.

Desired aspects of the present invention comprise crystals of NaCl salt or the like to be encapsulated by the polymerizing scaffold and which dissolve upon solidification of the material. The use of finely crushed ice particles made of specific intermediates such as frozen saline and collagen or gelatin can also be employed. Further, these can act as nucleating agents, preferably of temporary existence, which are able to initiate formation of gas bubble nuclei for cell formation.

The following examples are meant to be illustrative of the present invention, but are in no way meant to be limiting.

EXAMPLE 1

A polymer system of the present invention was prepared by using NCO-terminated isocyanates as part A and all remaining intermediates such as OH-terminated polyols, chain extenders, catalysts and all other additive components composing part B. The polymer was delivered, foamed and cured in order to provide a useful biomaterial for the scaffold. Both FNCO and OH values needed for calculation of stoichiometry of polymerization were determined using conventional analytical techniques. The following ingredients were obtained and mixed in the manner set forth below:

(a) 4,4'-diphenylmethane diisocyanate ("MDI") was obtained as Mondur ML from Bayer AG, Pittsburgh, Pa. This product is provided in liquid form and includes a combination of 2,2' 2,4' and predominantly 4,4' isomers of MDI.

(b) Polytetramethylene ether glygols ("PTMEG") used alone or as a blend of two or more different molecular weights ("MW") e.g. 250 and 1000 daltons, were obtained from BASF Corporation, Mount Olive, N.J.

(c) A chain extender composition was prepared by blending of both 1,4-butanediol ("BDO") as a linear chain extender and trimethylol propane ("TMP") as a crosslinking chain extender. The TMP is chemically recognized as 2-ethyl-2(hydroxymethyl)-1,3 propane diol.

(d) A catalyst was prepared having both tin catalyst and DABCO triethylene diamine ("TEDA") components in a suitable and desirable ratio;

(e) carbonated water was used as blowing agent.

(f) A 2000 daltons MW poly(diethylene glycol adipate) polyester polyol, FOMREZ 11-56, was obtained from Witco Chemical Co., Oakland N.J.

The isocyanate quasi-prepolymer component, referred to as part A was prepared by reacting 94.5 g of 1:1 PTMEG 250:1000 polyols blend with 250.26 g of Mondur ML isocyanate by a drop-wise addition of the polyol blend into the liquid isocyanate in a stirred reaction kettle equipped with Nitrogen gas blanket inlet. The reaction temperature was brought to 30–80 degrees Celsius. The reaction mixture was then stirred and the contents reacted until a constant, calculated FNCO value was attained (2–4 hours). Upon completion, the reaction product was fully degassed at elevated temperature in vacuo and cooled to ambient temperature. The reaction provided a liquid MDI-PTMEG quasi prepolymer having FNCO of 21.7 percent.

Part B was made by combining chain extenders, biodegradable polyol (e.g. FOMREZ 11-56 as above), water (as a blowing agent) and a catalyst system. The mixture was stirred in a resin kettle at 40 to 60 degrees Celsius until fully blended and slowly cooled to the minimum temperature to maintain all components liquid at ambient temperature.

For assessing its reactivity and foaming efficiency, both components were filled, based on required stoichiometry ratio between the parts, into a two-barrel syringe system of the type used for delivering two-part glue systems or dental composites. The materials were brought together and mixed by a static mixer. The mixed material was delivered into Teflon-coated molds resembling the intended implants, free-rise foamed and cured at 35 to 45 degrees Celsius for a period of 2 hours. Upon demold, foam samples were placed in a 37 degrees Celsius and equilibrated at this temperature and ambient humidity for a period of 7 days prior testing.

All testing was performed in accordance with ASTM Testing Methodology and accepted standard laboratory procedures. Among others factors, the foam density, average poor size, load bearing capability and accelerated degradation was determined.

EXAMPLE 2

A two-component system based on aliphatic isocyanate quasi-prepolymer was created. The system was composed of hydrogenated MDI, HMDI (obtained as DESMODUR W from Bayer, Pittsburgh Pa.) and PCP-0200 as Part A and OH-terminated intermediates, utilizing blend of PCP-0240, 1,4-butane diol (BDO) TMP, water and catalysts as Part B. The PCP-0200 and -0240 were obtained from Union Carbide, Danbury Conn. The system: was formulated and prepared according to the procedures described in Example 1. The delayed action, low exotherm, and fast curing kinetics was achieved with a tin-compound/tertiary amine based catalyst system giving cream and gel times of 30–120 seconds, predominant cure of 2–5 minutes, and target in vivo exotherm not exceeding 70–90 Celsius.

The system was mixed, delivered, foamed, cured and shaped to form the polyurethane scaffold. Chemical cross-linking, often required for improvement of overall strength of such relatively soft materials, with solid state hardness of 60–95 Shore A, was accomplished by the blend of BDO and TMP chain extenders, in a ratio from 3:1 to 1:3. Controlled biodegradability was achieved by the use of lysis-prone PCP-0200 and PCP-0240 polycaprolactone polyols. The concentration of water blowing agent and Isocyanate Index (II), which is the ratio of NCO- to OH- and/or amine-terminal groups, was varied to produce foams of different density and pore sizes.

EXAMPLE 3

To illustrate the influence of water concentration on the density and cell size of the foam, a system was formulated based on 5:1 isocyanate quasi-prepolymer of HMDI and TMP, BDO as chain extender, FOMREZ 11-56 (diethylene glycol adipate) as the soft segment and carbonated water as blowing agent. These materials were based on 50 percent of HMDI based quasi-prepolymer/BDO hard segment and 1, 3, 5 and 7 percent of water (compositions 2–5), added to the soft segment polyol. First, the TMP, kept at 65 degrees Celsius was added drop-wise to the 40–70 degrees Celsius warm HMDI isocyanate and reacted as in Example 1. The final quasi-prepolymer, coded H12/TMP, contained 15 weight percent of TMP and had the Free NCO-group concentration of 20.35 percent and equivalent weight of 206.38 g/eq. This quasi-prepolymer represents the part A. The FOMREZ 11-56 polyol was then mixed with required amounts of carbonated water blowing agent, the BDO chain extender, and an amine catalyst, constituting part B of the polymer.

Table I shows various compositions and the relative amounts of their components for approximately 1000 g batches.

TABLE I

| | Composition | | | | |
|---|---|---|---|---|---|
| COMPONENT | 1 | 2 | 3 | 4 | 5 |
| FOMREZ 11-56 (g) | 427.3 | 427.3 | 427.3 | 427.3 | 427.3 |
| WATER (g) | 0.0 | 10.0 | 30.0 | 50.0 | 70.0 |
| POL/WATER[1] EQ. WT. (g/eq) | 1,001.78 | 976.84 | 934.22 | 897.03 | 866.80 |
| POL/WATER[2] EQV'S | 0.4265 | 0.4370 | 0.4570 | 0.4760 | 0.4930 |
| BDO (g) | 86.9 | 86.9 | 86.9 | 86.9 | 86.9 |
| BDO EQV'S | 1,929 | 1.929 | 1.929 | 1.929 | 1.929 |
| OH-EQV,S | 2.36 | 2.375 | 2.39 | 2.405 | 2.422 |
| H12/TMP (g)[3] 100 IsocIndex | 486.1 | 489.1 | 493.3 | 496.4 | 499.9 |
| CAT (%)[4] | ~0.6 | ~0.6 | ~0.6 | ~0.6 | ~0.6 |
| CREAM (sec)[5] | N.A. | 1.5–2.0 | 3.5–4.0 | 5.0 | 5.0 |
| GEL (sec) | 40–60 | N.A. | N.A. | N.A. | N.A. |
| TACK FREE | ~1 min | ~10 min | ~10 min | ~7.0 min | ~7.0 min |
| % POROSITY[6] | ~0.0 | ~10.0 | ~40–50 | ~60–70 | ~85+ |
| AP.DENSITY[7] (g/ccm) | 1.24 | 1.08 | 0.68 | 0.43 | 0.19 |
| PORES (microns) | N.A. | ~40–60 | 100–200 | 200+ | UNEVEN |

[1]Polyol/water composition equivalent wt.
[2]Polyol/water equivalents.
[3]H12 MDI/TMP quasi-prepolymer.
[4]Catalyst TEDA.
[5]Cream time - physical gelation of foam.
[6]Measured by the weight difference before and after foaming.
[7]AP.DENSITY = Approximate density

EXAMPLE 4

To demonstrate the influence of Isocyanate Index (II) on foam density, a model system based on high MW, yet liquid polyol was formulated using high functionality polyethylene oxide capped polyol (VORANOL CP4711, MW~6000 daltons, Dow Chemical Co. Midland Mich.). An 100 parts by weight (pbw) with 3.5 pbw of water as blowing agent, 0.6 pbw of amine catalyst and RUBINATE M (liquid, modified MDI, ICI Urethanes, West Deptfort, N.J.) as isocyanate. By variation of II at 80, 100 and 120 the foams with density of approximately 0.045, 0.050 and 0.055 g/ccm were produced at 5 minutes demold time.

EXAMPLE 5

The method of T.M.S. Chang (U.S. Pat. No. 5,084,350) was used for microencapsulation of living cells as biologically active materials. As a model, the hepatocytes-containing artificial cells for xenograft transplantation and hepatic replacement were chosen.

In order to prevent clumping, aggregations and fibrous formations after implantation the membrane materials have been produced with the following characteristics. The microstructure is permeable for the diffusion of nutrients or metabolites of the encapsulated cells or biologically active material. At the same time, the microstructure is impermeable to the host immune system proteins or cells, thus preventing immunological rejection:

In this method, hepatocytes were encapsulated within a semipermeable capsule formed by thermally reversible polyvinyl alcohol (PVAL) hydrogel on beads of gelled solution, prepared by suspending the cells in a solution of a water-soluble alginates, which was reversibly gelled by calcium ions, forming the said solution into droplets and gelling the droplets to produce discretely shaped gelled beads. Formation of semi-permeable membrane from thermally reversible solution of PVAL on each of the gelled beads prevents the incorporation of any biologically active material into the membranes and allows for "on demand" reliquefication of the cells encapsulating gel and redispersing the cells within the membrane-covered beads. Many materials could be used for this process and their selection depends on each individual application.

The resultant encapsulated cells were then incorporated into compositions 3 and 4 of Table I.

EXAMPLE 6

Mouse fibroblast I-929 cells were dispersed in a buffered n-saline and low MW PVAL solution, emulsified with a few drops of medical grade silicone oil and deep-frozen to −20 degrees C. while gently agitated to form ice-beads-like particulate matter. The said matter could be stored at frozen state as needed. Upon application, the frozen matter was slowly thawed to room temperature while allowing the PVAL to reversibly gel and form semipermeable membrane over the formed beads. Such encapsulated cells were ready for formation of mix-in stream within the porous scaffold formation system.

EXAMPLE 7

The in situ cured polyurethane scaffold as described in Example 1 was evaluated for in vivo restoration of damaged articulating cartilage, without addition of encapsulated cells, in a young sheep model and exhibited excellent biocompatibility and propensity for cartilage repair. The compositions, when cured, exhibit desirable physical characteristics, particularly relating to conformational stability and retention of physical shape, desirable mechanical properties e.g. load-bearing strength and impact absorption.

Various changes to the foregoing described and shown methods would now be evident to those skilled in the art. Accordingly, the particularly disclosed scope of the invention is set forth in the following claims.

What is claimed is:

1. A method for in vivo tissue engineering comprising the steps of:
   (1) combining one or more components of a flowable biocompatible polymerizable composition including an effective amount of a blowing agent in a reaction injection mixing device; and
   (2) delivering the resultant combination to a body site via a scope-assisted minimally invasive technique, whereby said effective amount of blowing agent permits said polymerizable composition to cure in vivo to form a porous foamed polymer structure which permits cellular ingrowth.

2. The method of claim 1 wherein the reaction products of said polymerizable composition is a biodegradable polymer.

3. The method of claim 1 wherein said polymerizable composition is formed into a desired shape in vivo prior to cure.

4. The method of claim 1 wherein said cured polymerizable composition is a microcellular structure.

5. The method of claim 1 wherein said cured polymerizable composition is in the shape of a film or membrane.

6. The method of claim 1 wherein said polymerizable composition forms a biodegradable cell scaffold in vivo for regeneration of tissue.

7. The method of claim 1, further including adding to the polymerizable composition seed cells, which remain viable subsequent to cure of said polymerizable composition.

8. The method of claim 7, wherein said seed cells are separately encapsulated in a biodegradable material.

9. The method of claim 8 wherein said seed cells are attached via a biodegradable tether to said cured polymer.

10. The method of claim 7 wherein said seed cells are stem cells.

11. The method of claim 7 wherein said seed cells are transgenic cells.

12. The method of claim 1 wherein said body site is soft tissue.

13. The method of claim 1 wherein said body site is hard tissue.

14. The method of claim 1 wherein said cured polymer comprises a polyurethane block copolymer.

15. The method of claim 1 wherein said cured polymer comprises soft and hard segments.

16. The method of claim 1 wherein said combining further includes bioactive agents.

* * * * *